United States Patent [19]

Oye

[11] 4,451,234
[45] May 29, 1984

[54] DENTAL ARTICULATOR DEVICE

[76] Inventor: Toshimi Oye, Pitman Jefferson Rd., Mullica Hill, N.J. 08062

[21] Appl. No.: 441,084

[22] Filed: Nov. 12, 1982

[51] Int. Cl.³ .............................................. A61C 11/00
[52] U.S. Cl. ...................................................... 433/54
[58] Field of Search ..................................... 433/54, 60

[56] References Cited

U.S. PATENT DOCUMENTS 3,466,750 9/1969 Timberlake et al. .................. 433/54
4,207,677 6/1980 Lampert ................................ 433/54

FOREIGN PATENT DOCUMENTS 1124255 10/1956 France .................................. 433/54

Primary Examiner—Robert Peshock
Attorney, Agent, or Firm—Thomas A. Lennox

[57] ABSTRACT

The dental articulator device of this invention includes a lower tongue member device to receive and hold a model of the mandibular portion of the pair and an upper tongue member device to receive and hold a model of the maxillary portion of the jaw. A lower body device is provided for providing support for holding the device and structurally connecting it to the lower tongue member.

11 Claims, 3 Drawing Figures

DENTAL ARTICULATOR DEVICE

BACKGROUND OF THE INVENTION

This invention involves dental articulators for holding models of the patient's mouth, generally involving the construction of false teeth, and in particular bridge work.

When the necessity arises for the constructing and inserting bridge work to replace one or more teeth, an impression of the mouth is made followed by a casting representing the present condition of the mouth. Bridge work is designed and constructed to fit into the mouth by highly skilled individuals. In order to insure proper fitting the proposed bridge work is installed into the casting, representing the mouth of the patient. Bite registration is provided from the dentist to make the molds. Dental model articulators are used to hold the castings of the maxillary (upper) jaw portion and the mandibular (lower) jaw portion. The articulator is used to hold the maxillary and the mandibular in position to illustrate how the teeth intermesh. One purpose of the articulator is to make sure that upon closure of the teeth, all of the strain is not placed on the new bridge, but rather distributed throughout the mouth, teeth to teeth contact. Such articulators are described below.

One of the particular problems with the present articulators is that they do not allow excursive movement of the jaw along the "Curve of Spee" in a fashion to duplicate the relative movements of the jaw and the intermeshing of the teeth during the lateral movement of chewing activity. It has been found that a bridge might be properly placed and of satisfactory size when the models of the upper and lower jaw are intermeshed by vertical movement, but that substantial obstruction and difficulties arise when the patient attempts to chew in a side to side movement to masticate the food. A great need has arisen to provide an articulator which will essentially duplicate the relative movement of the jaw models during the chewing activity. Articulators that do not satisfy these and other objects of this invention include the articulator described in U.S. Pat. No. 4,207,677 to Gary Lampert, and other older versions including U.S. Pat. No. 3,823,476 to Robert C. Hudson, et al., U.S. Pat. No. 3,727,311 to Andre T. Schoonebek, U.S. Pat. No. 3,466,750 to Dale L. Timberlake, and U.S. Pat. No. 2,556,639 to Elver B. Wimberly.

SUMMARY OF THE INVENTION

An object of the invention is to provide a dental model articulator which is capable of duplicating the "Curve of Spee," that is the excursive jaw movement during the chewing process.

It is a particular object of this invention to provide a dental model articulator which allows testing new bridge work in the model under movement conditions that approximate actual jaw movements.

An additional object of this invention is to provide a dental model articulator that allows varying the position of the upper jaw holder in the horizontal direction, both upwardly and downwardly from the normal positioning.

An additional object of this invention is to provide a dental model articulator capable of easy attachment to a table or to be held in the hands.

A further object of this invention is to provide a dental model articulator with a stop position to approximate the horizontal level of the upper maxillary jaw position.

It is an additional object of this invention to provide in addition to the horizontal stop position, the ability to position the maxillary jaw portion at any radial angle an have it remain in that position.

An additional object of this invention is to provide for lateral movement of the dental models respective to each other with increased resistance as further movement is attempted from the horizontal plane.

A particular object of this invention is to provide an articulator with internal mechanisms for guiding and control of the movement of the model holders rather than the external hinges, springs and guides of the prior devices that tend to become corroded, adulterated and inoperative with use.

The dental articulator device of this invention includes a lower tongue member device to receive and hold a model of the mandibular portion of the jaw and an upper tongue member device to receive an hold a model of the maxillary portion of the jaw. A lower body device providing support for holding the device and structurally connecting it to the lower tongue member is provided. An articulator member device is structurally attached to and extends from the lower body means in a generally vertical direction, wherein the articulator member device includes a member of a cross sectional shape and material to allow twisting movement of the upper tongue member to simulate excursive movement of the jaw along a path of least resistance. An attachment device is provided hingably attaching the upper end of the articulator member to a near end of the upper tongue member means to allow vertical movement of the outer end of the upper tongue member in relation to the balance of the dental model articulator device.

DESCRIPTION OF PREFERRED EMBODIMENTS

Figure 1:
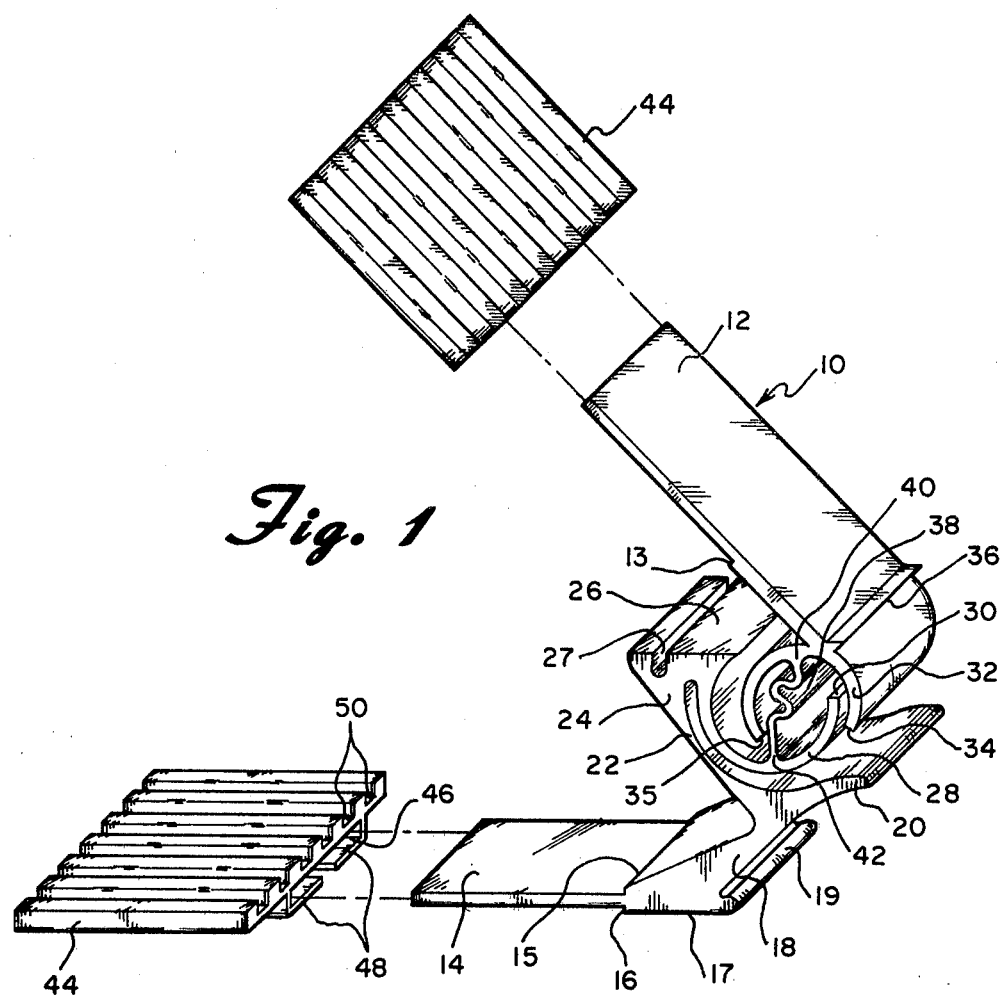
FIG. 1 is a perspective view of the dental articulator of this invention, illustrating the parts disengaged and including shoe plates for holding the teeth and jaw reproductions in alignment to be positioned on the articulator.

The dental model articulator 10 as illustrated in FIG. 1 is preferably constructed of a thermoplastic polymer such as the group generally known in the industry as engineering plastics. Articulator 10 may certainly be constructed of metal or any suitable material, but as referred to above and as will be apparent from the entire specification, the shape and thickness of the particular elements of the device will vary considerably depending upon the elasticity and flexural moduli of the material. It is preferred that articulator 10 be injection molded of an engineering thermoplastic polymer, but as may be observed, it is possible to extrude the part as it may be constructed in a single cross-sectional shape.

Figure 2:
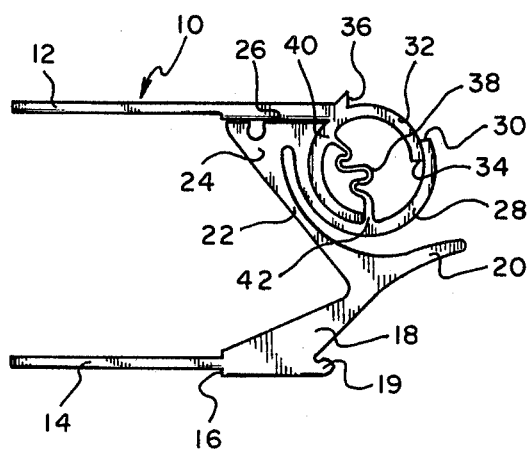
FIG. 2 is a side view of the articulator illustrated in FIG. 1, illustrating engagement of the socket attachment with the upper tongue member in the horizontal position.
Figure 3:
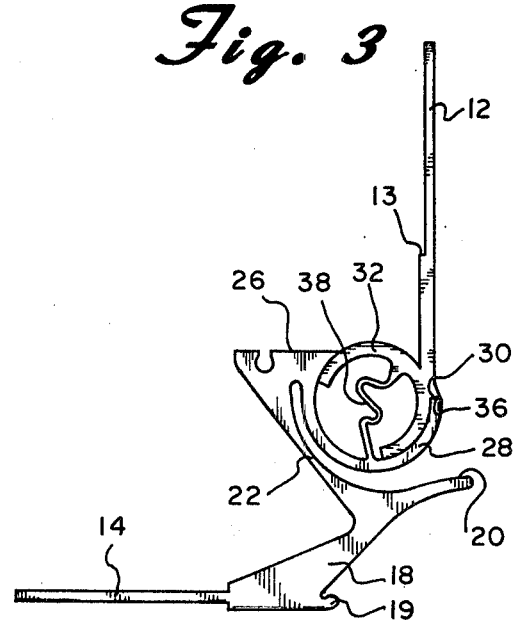
FIG. 3 is a second side view of the articulator illustrated in FIG. 1, with the upper tongue member moved to the vertical position.

As pictured in FIG. 1, articulator device 10 includes upper tongue member 12 designed to be positioned in a horizontal plane and lower tongue member 14 designed to rest on a horizontal surface, such as a work table. Each tongue is designed to receive a shoe plate 44 onto which is positioned a reproduction of the teeth and jaw. Upper member 12 holds the maxillary jaw portion. Stop 13 on tongue 12 positively positions shoe plate 44 and stops 15 and 16 position an identical plate 44 on lower member 14. Lower shoe member 14 provides a cutout portion on its lower side such that base 17 is actually the only area of contact where device 10 touches the work table. Plates 44 will slide onto and attach to upper and lower tongues 12 and 14, as will be described below, and fit into that space to provide a flat resting area for articulator device 10. Thus, when plate 44 for the lower shoe member 14 slides onto the tongue shape, the plate provides a one plane resting area for the front end of the lower shoe member. Structurally attached to member 14 is upright, rigid support 18, of sufficient thickness that there is little or no flexibility of that support upon movement of the upper parts. Protrusion 19 is included to allow device 10 to be wedged under a convenient edge to hold the device in place. Directly attached to support 18 is holding arm 20, again of a thickness and attachment strength that there is little flexibility in this part of the device when held by the hand. An additional purpose of arm 30 is to support a wedge which may be forced between arm 20 and socket 28 to compensate for front or back positioning of the models. For example, the above wedge will tend to raise the rear of tongue 12 and lower the front of tongue 12, so that the front of the teeth will be closer together in the case of incorrect positioning. Articulator member 22 is a thinner extension member connected to support 18 extending generally in an upwardly direction and having at least some vertical positioning. As illustrated, the articulator of FIG. 1 utilizes articulator member 22 at about a 60 degree angle from the horizontal. This articulator angle, together with the thickness and cross-sectional shape of the member, together with the material of construction of the member, all affect the performance of this member. As the angle of member 22 is lowered toward the horizontal, the degree of flexibility of a twisting action in the horizontal plane is reduced. As the angle is increased toward the vertical, the ease of flexibility of the twisting movement is increased. The angle from the horizontal for articulator member 22 is preferably in the range of 10 to 80 degrees, more preferably in the range of 20 to 75 degrees, even more preferably in the range of 30 to 70 degrees, and most preferably about 55 to 65 degrees from the horizontal. Likewise, as a cross-sectional area, articulator member 22 is decreased, and as the shape approaches a thin long rectangle, the flexibility is increased. Clearly, the flexural modulus of the material chosen to construct articulator member 22 will affect this ease of twisting movement to provide articulation of the models held on tongue members 12 and 14. Choice of a combination of these variables in the construction of articulator member 22 allows the twisting movement along the path of least resistance to simulate the "Curve of Spee". The choice of material and the dimension of articulator 10 in general and member 22 in particular, can be designed by computer or aided in design by computers to provide the physical properties necessary to carry out the advantages of this device at the best level. The properties of the material include degree of rigidity, brittleness, ductility and the like. Structurally attached to articulator member 22 is horizontal stop member 24, providing a resting position and firm support for upper shoe member 12 on horizontal stop surface 26. Structurally attached and depending from member 24 is a partial cylindrical tube socket member 28 with a longitudinal opening on the top. Socket 28 includes more than 180 degrees of the cylinder and is preferably about 270 degrees, with about a 90 degree opening in the tube. The material of construction for socket 28 allows for certain ductility and allows drum member 32 to be snapped past edge 30 of the opening to socket 28. Drum member 32 is again a partial cylindrical tube having a longitudinal cutout of about 90 degrees, leaving about 270 degrees remaining of the cylindrical tube drum member 32. Edges 34 and 35 of drum member 32 are flexed inwardly as drum member 32 is snapped into the socket of cylindrical socket 28. The outside diameter of drum member 32 is chosen to be equal to or slightly larger than the inside diameter of socket member 28, so as to provide a spring action between the mating surfaces. This allows positioning of drum 32 at any chosen position in a positive hold in any radial position. Slot 27 is provided to allow tightening socket 28 by wedging an object into the slot, or in the alternative, to change the angle of stop surface 26 by inserting a wedge into the slot. Upper shoe member 12 is structurally attached tangentially to drum member 32 such that it may rest on surface 26 while allowing drum 32 to seat firmly in socket 28, as illustrated in FIG. 2. Raised stop ridge 36 is placed on the exterior surface of drum member 32 and positioned to abut and stop further rotation of drum 32 when stop 36 meets edge 30, placing upper shoe member 12 in an essentially vertical position, as illustrated in FIG. 3. Connection bias member 38 is a thin ductile elastic piece molded in a curling shape such that vertical movement is essentially unimpeded, but horizontal movement of drum 32 inside socket 30 is prevented. Bias member 38 is attached to the inside of drum 32 at point 40 and to the inside of socket 28 at point 42. These points are chosen so that in any vertical turning position of drum 32, the opening in drum 32 allows its edges not to come in contact with bias member 38.

Shoe plate 44 is equipped to slide onto and hold in position on tongues 12 and 14, as illustrated in FIG. 1. Cavity channel 46 runs the length of plate 44 as the stops on each tongue position the plate. Spring holders 48, in the shape of inverted "L" shapes, converge at the center to form the cavity 46, which is shaped to provide a snug fit on tongues 12 and 14. Grooves 50 are provided on the working face of shoe plate 44 to provide extra connection between the casting material and the plate. This surface may be constructed in a variety of shapes so long as good adhesion is achieved with the casting material.

It is preferred that the plates are capable of easily detachable attachment to the tongue and have a ridged surface to provide good adhesion to the plaster material. As mentioned above, articulator 10 allows movement of the jaw to simulate the excursive movement of the jaw, the movement along the upper teeth line known in the trade as the "Curve of Spee," this angle being approximately 20 degrees from the horizontal, or about one quarter one half of inch movement in the vertical direction. This angle has also been known as the angle of cuspation. The articulator member design allows the movement along the path of least resistance as horizontal force is applied to the maxillary model, to cause it to move to approximate the "Curve of Spee," rather than in an exact horizontal plane. The typical movement above the horizontal along the "Curve of Spee" is approximately 20 degrees from the horizontal, but may be in the range of 10 to 30 degrees. The flexibility of articulator 10 allows easy movement along this range of curves.

A preferred embodiment of the present invention is a dental model articulator device including a lower tongue member and an upper tongue member, each of which is designed to receive a shoe plate, detachably attached to the shoe member to attach to and carry the upper and lower jaw models respectively for articulation. Attached to the lower tongue member is a rigid upright support member structurally attached and extending from the lower shoe member. This support member preferably has little or no flexibility. An articulator member is structurally attached and extends from the upright support member. This articulator member is constructed such that it and all parts of the device attached to it may be twisted in an essentially horizontal plane. This is accomplished by constructing the articulator member of a combination of cross-sectional shape and material so that the articulator member, extending in a generally upward direction may be subjected to substantial twisting movement in an essentially horizontal plane. A horizontal stop member is structurally connected to the top of the articulator member providing a resting place for the upper shoe member when it is placed in a horizontal position. A partial horizontally placed cylindrical socket member is structurally attached and depends from the stop member. A mating partial horizontally placed cylindrical hollow drum member is structurally attached to the rear of the upper shoe member. The drum and socket combination is sized to allow an interfitting relationship such that the diameter of the drum member is a slightly larger diameter than the socket member such that when the drum member is snapped into the socket member, the tight fit allows turning movement of the drum in the socket, but holds the position of the drum at any chosen radial angle stopping position. A ribbon connection member connects the inside surface of the socket and the inside surface of the drum at points on each part where the cylinders are each not complete. The socket and drum members may also be described as partial cylindrical tubes wherein a longitudinal slice is removed out of each. This construction allows for springable resistance upon compression on the outside of the drum and springable resistance upon pressure on the inside of the socket, providing a close fit and a positive holding position of the drum and thus the upper shoe member.

While this invention has been described with reference to the specific embodiments disclosed herein, it is not confined to the details set forth and the patent is intended to include modifications and changes which may come within and extend from the following claims.

I claim:

1. A dental articulator device comprising:
   (a) a lower tongue member means to receive and hold a model of the mandibular portion of the jaw,
   (b) an upper tongue member means to receive and hold a model of the maxillary portion of the jaw,
   (c) a lower body means providing support for holding the device and structurally connecting it to the lower tongue member,
   (d) an articulator member means structurally attached and extending from the lower body means in a generally vertical direction, wherein the articulator member means comprises a member of cross sectional shape and material to allow twisting movement of the upper tongue member to simulate excursive movement of the jaw along a path of least resistance, and
   (e) an attachment means hingably attaching the upper end of the articulator member means to a near end of the upper tongue member means to allow vertical movement of the outer end of the upper tongue member in relation to the balance of the dental model articulator device wherein the attachment means comprises
      (i) a horizontal partial cylindrical socket member, attached to the upper end of the articulator member, and
      (ii) a horizontal partial cylindrical hollow drum member structurally attached to the rear of the upper tongue member,
      wherein the drum member fits into and is of the same size or slightly larger diameter than the socket member, such that when the drum member is snapped in, the snug fit allows turning movement of the drum in the socket but holds the position at any chosen radial angle.

2. The device of claim 1 wherein the twisting movement of the articulator member is in an essentially horizontal plane.

3. The device of claim 1 wherein a horizontal stop member is structurally connected to the top of the articulator member, providing a resting place for the upper tongue member.

4. The device of claim 1 wherein a ribbon connection means connects the inside surface of socket and the inside surface of the drum at points where the cylinders are each not complete.

5. The device of claim 4 wherein the ribbon connection means comprises a curled thin elastic member of sufficient width to prevent longitudinal movement of the drum member with respect to the socket member.

6. The device of claim 1 wherein each shoe is provided with a plate capable of detachable attachment to the shoe and having a ridged surface in contact with the model.

7. The device of claim 1 wherein an upright rigid support member is structurally attached and extending from the lower shoe member and to which the articulator member means is structurally attached.

8. The device of claim 7 wherein a rigid horizontal holding arm extension is structurally attached to the upright support member.

9. A dental model articulator device comprising:
   (a) a lower tongue member means,
   (b) a body means structurally attached to the lower tongue member means providing a supporting surface such that the device can rest on a horizontal surface and comprising an upright rigid support member structurally attached and extending from the lower tongue member means,
   (c) an articulator member means structurally attached and extending from the upright member,
   wherein the articulator member means comprises an articulator member extending in a generally upwardly direction constructed of a combination of cross-sectional shape and material so as to allow twisting movement along a path of least resistance to simulate excursive movement of the human jaw,
   (d) a horizontal stop member structurally connected to the top of the articulator member defining a resting position for the upper tongue member means, (e) a partial horizontal cylindrical socket member depending from the stop member, (f) a partial horizontal cylindrical hollow drum member structurally attached to the rear of the upper tongue member means, wherein the drum members of a size and shape to fit into the socket member, and (g) a connection means between the drum and socket members to prevent longitudinal movement between the two parts.

10. The device of claim 9 wherein the size and shape of the drum member is essentially the same size or slightly larger in diameter to the socket member so as to create a snug fit where the parts are interfitted.

11. The device of claim 9 wherein the connection means comprises a ribbon connection between the inside surfaces of the socket and the drum.

* * * * *